United States Patent
Lee

(10) Patent No.: US 12,310,618 B1
(45) Date of Patent: May 27, 2025

(54) ULTRASOUND PROBE DETACHABLE INJECTION ASSISTANT

(71) Applicant: Young Chul Lee, Busan (KR)

(72) Inventor: Young Chul Lee, Busan (KR)

( * ) Notice: Subject to any disclaimer, the term of this patent is extended or adjusted under 35 U.S.C. 154(b) by 0 days.

(21) Appl. No.: 19/057,001

(22) Filed: Feb. 19, 2025

(30) Foreign Application Priority Data

Apr. 30, 2024 (KR) .................. 10-2024-0057952

(51) Int. Cl.
*A61B 17/34* (2006.01)
*A61B 8/00* (2006.01)
*A61B 8/08* (2006.01)

(52) U.S. Cl.
CPC ............ *A61B 17/34* (2013.01); *A61B 8/0841* (2013.01); *A61B 8/4444* (2013.01); *A61B 2017/3413* (2013.01)

(58) Field of Classification Search
CPC ..... A61B 17/34; A61B 8/0841; A61B 8/4444; A61B 2017/3413; A61B 2017/2253; A61G 13/127; B05B 17/06; G01S 7/52079
See application file for complete search history.

(56) References Cited

U.S. PATENT DOCUMENTS

| | | | | |
|---|---|---|---|---|
| 2013/0263438 A1* | 10/2013 | Burns | ...................... | A61B 8/58 16/422 |
| 2014/0276081 A1* | 9/2014 | Tegels | .................. | A61B 8/4209 600/461 |
| 2019/0069923 A1* | 3/2019 | Wang | .................. | A61B 8/0841 |

FOREIGN PATENT DOCUMENTS

| | | |
|---|---|---|
| CN | 205286423 U | 6/2016 |
| CN | 211381439 U | 9/2020 |
| JP | 2005034273 A | 2/2005 |
| JP | 2009291387 A | 12/2009 |
| JP | 2010068923 A | 4/2010 |
| KR | 20170037584 A | 4/2017 |
| KR | 20180000523 A | 1/2018 |
| KR | 20190031732 A | 3/2019 |
| KR | 20200668881 A | 6/2020 |

* cited by examiner

*Primary Examiner* — Amal Aly Farag
(74) *Attorney, Agent, or Firm* — NKL Law; Jae Youn Kim

(57) ABSTRACT

The Present invention relates to an ultrasound probe detachable injection assistant. A structure of the ultrasound probe detachable injection assistant of the present invention, comprising: a probe fixture for holding the probe, wherein the probe fixture wraps around a portion of outer circumferential surface of the probe and is capable of securing the probe, wherein the probe fixture is formed by a first body portion and a second body portion coupled by a first connecting portion and a second connecting portion, wherein the first body portion and the second body portion each being adjustable in length so as to wrap around outer circumference of the probe when coupled, a plurality of needle guides for inserting and holding a syringe, and hingedly coupling with the probe fixture to allow adjustment of an injection angle of the syringe, a bump formed on the needle guides for coupling the needle guides with the probe fixture, a receiving groove formed on at least one outer circumferential surface of the probe fixture to allow the bumps to couple.

5 Claims, 13 Drawing Sheets

ULTRASOUND PROBE DETACHABLE INJECTION ASSISTANT

TECHNICAL FIELD

The present disclosure relates to an ultrasound probe detachable injection assistant, and more particularly to a device for attaching to an ultrasound probe (handle) used in intervention using ultrasonography to insert a shake-free injection.

BACKGROUND ART

Although the diagnosis of diseases has become more accurate with the advancement of medical devices, the method of injection using a syringe and its efficacy can vary depending on the ability and discretion of each medical professional.

When performing injection intervention in the human body, the depth, angle, and direction of insertion are important, and if the medical professional's skill level is low, he or she may not be able to insert the syringe needle exactly where it should enter the body, or may make multiple mistakes, depending on the patient or intervention (examination) environment.

Furthermore, during any injection process, it is essential to determine whether the needle tip of the syringe is or is not injected into a blood vessel. To ensure this, it is necessary to have a clear view of the direction of the needle, which may require the medical professional to change the position or orientation of the hand holding the syringe during the process of filling the syringe with medicine then injecting it into the body. However, when the syringe is held differently as described above, a slight shaking may occur, which often results in failure to inject the medicine in the correct location or painful sensations for the recipient.

In addition, in the process of performing intervention using ultrasonography, even if histologic examination and injection are performed at the same time, there were problems such as the inability to see the syringe needle in the tissue or the inaccuracy of the injection intervention due to the focus on ultrasound.

Therefore, a specific method to solve these problems is required.

SUMMARY

The ultrasound probe detachable injection assistant according to the present disclosure aims to solve the problems by providing a structure in which a fixture with a syringe rail attached or detached can be fixed to an ultrasound probe, and in which the syringe rail can be selectively detached from the fixture as needed due to the presence of various angles of the syringe rail, but in which the fixture has a plurality of sites (front, back, left, right) in which the syringe rail can be detached.

To achieve the solve the above problem, a probe detachable injection assistant according to the present disclosure, including: a probe fixture for holding a probe, the probe fixture wrapping around a portion of an outer circumferential surface of the probe, the probe fixture being capable of holding the probe, the probe fixture being formed by coupling a first body portion; and a second body portion; by the first connecting portion and the second connecting portion, wherein the first body portion and the second body portion, when coupled, are each adjustable in length to wrap around the outer circumferential surface of the probe, and wherein a syringe is inserted and secured, a plurality of needle guides hingedly coupled with the probe fixture to allow adjustment of an injection angle of the syringe, a bump formed on the needle guides for engagement of the needle guides with the probe fixture, and at least one receiving groove formed on an outer circumferential surface of the probe fixture to allow the bump to engage.

Additionally, wherein, the needle guides may further include a rail into which the syringe is inserted, formed for adjusting the depth of insertion to adjust the depth of injection into the human body, and a plurality of protrusions formed along the inner circumferential surface of the rail to facilitate the insertion of the syringe.

Additionally, wherein, the receiving groove is horizontally movable along the outer circumferential surface of the probe fixture.

Additionally, wherein, the lower portion of the needle guides is retractable.

Additionally, wherein, the protrusion includes a structure that allows air to enter the interior, such that the size of the interior space of the rail can change as the protrusion expands and contracts.

Additionally, wherein, the bump moves along the guide formed in the receiving groove, and a sliding engagement may be made between the bump and the receiving groove.

To achieve the solve the above problem, a second probe detachable injection assistant according to the present disclosure, including: a second probe fixture for gripping a probe along a lower outer circumferential surface and holding the probe, the second probe fixture being formed by coupling a first frame with a second frame, at least one second needle guide formed on one side of the second probe fixture and included for holding a needle of a syringe, the second needle guide may further include an angle adjustment device for adjusting an angle of injection.

Advantageous Effects

The ultrasound probe detachable injection assistant according to the present disclosure has the effect that the user can use the ultrasound probe without any inconvenience or difficulty even if the device is still attached to the ultrasound probe, so that the user does not have to repeatedly perform the operation of attaching and detaching the device during busy clinic hours.

In addition, the detachable needle guides are available in several types of angles, allowing the user to select the needle guide according to the depth required, making it quick and easy to use without complicated maneuvers.

It also has the effect of making it easier to insert a syringe into narrow or curved areas of the body.

Furthermore, in the process of filling the syringe with medicine then injecting it into the body, shaking may not occur even if the position or direction of the hand holding the syringe is changed, thus enabling accurate injection and preventing painful situations for the recipient.

The effects of the present disclosure are not limited by the above, and various other effects are included in this specification.

BRIEF DESCRIPTION OF THE DRAWINGS

The embodiments of the present specification will be better understood with reference to the following description in conjunction with the accompanying drawings, in which like reference numerals refer to identical or functionally similar elements.

Figure 1:
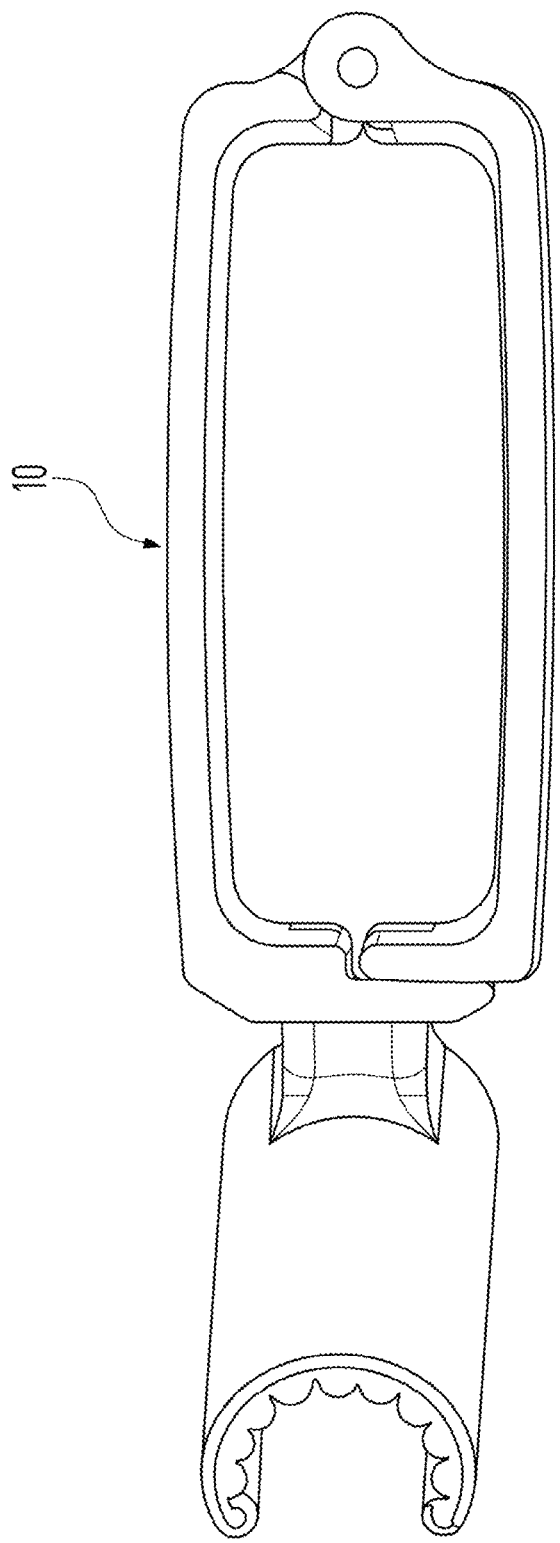
FIG. 1 is a top view of a probe detachable injection assistant according to one embodiment of the present disclosure.

It is to be understood that the above referenced drawings are not necessarily shown to scale, but rather present a rather simplified representation of various preferred features that exemplify the basic principles of the present disclosure. For example, certain design features of the present disclosure, including specific dimensions, orientations, locations, and shapes, will be determined in part by the specific intended application and environment of use.

DETAILED DESCRIPTION

Hereinafter, some embodiments of the present disclosure will be described in detail with reference to the exemplary drawings. In assigning reference numerals to the components in each drawing, the same components may have the same numeral to the extent possible, even though they are shown in different drawings.

In addition, in describing the embodiments, specific descriptions of related disclosed configurations or features may be omitted if it is determined that such detailed description would obscure the essence of the present technical ideas.

Wherever the words "includes," "has," "consists of," "consists of" or the like are used herein, other parts may be added unless "only" is used. Where components are expressed in the singular, the plural is included unless otherwise expressly stated.

In addition, terms such as first, second, A, B, (a), (b), and the like may be used to describe components of the present disclosure. Such terms are intended only to distinguish one component from another, and the nature, sequence, order, or number of such components is not limited by such terms.

In a description of the positional relationship of components, when two or more components are described as being "connected," "coupled," or "combined," etc., it is to be understood that the two or more components may be directly "connected," "coupled," or "combined," but may also be "connected," "coupled," or "combined" other components that are further "interposed" with the two or more components.

Here, other components may be included in one or more of two or more components that are "connected," "coupled," or "combined" to each other. In descriptions of temporal flow relationships with respect to components, methods of operation, methods of fabrication, and the like, for example, where a temporal antecedent or flow antecedent relationship is described as "after," "following," "next to," "before," or the like, it may include instances that are not consecutive unless "immediately" or "directly" is used.

Hereinafter, the present disclosure will be described in more detail with reference to the following embodiments of the invention.

Figure 2:
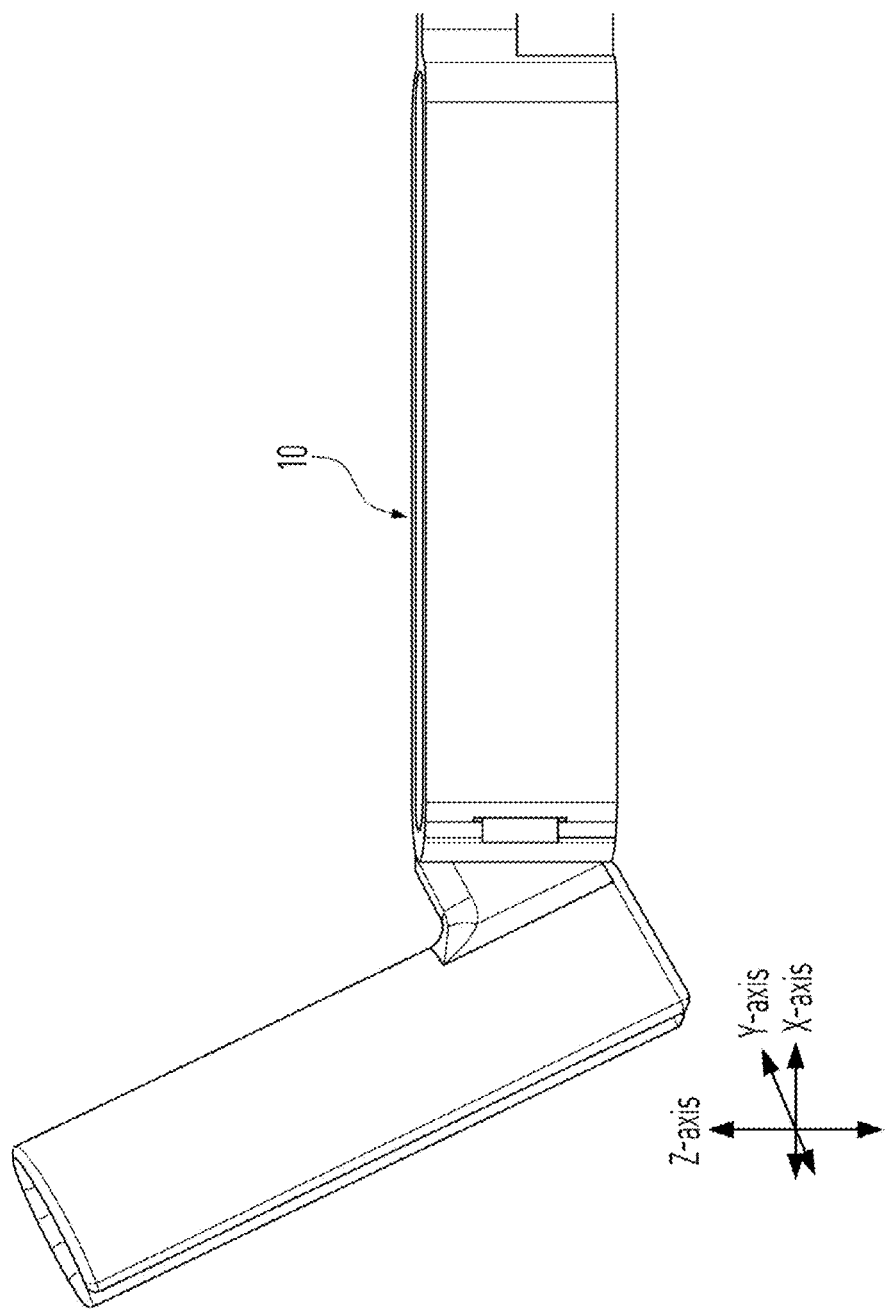
FIG. 2 is a side view of a probe detachable injection assistant according to one embodiment of the present disclosure.
Figure 3:
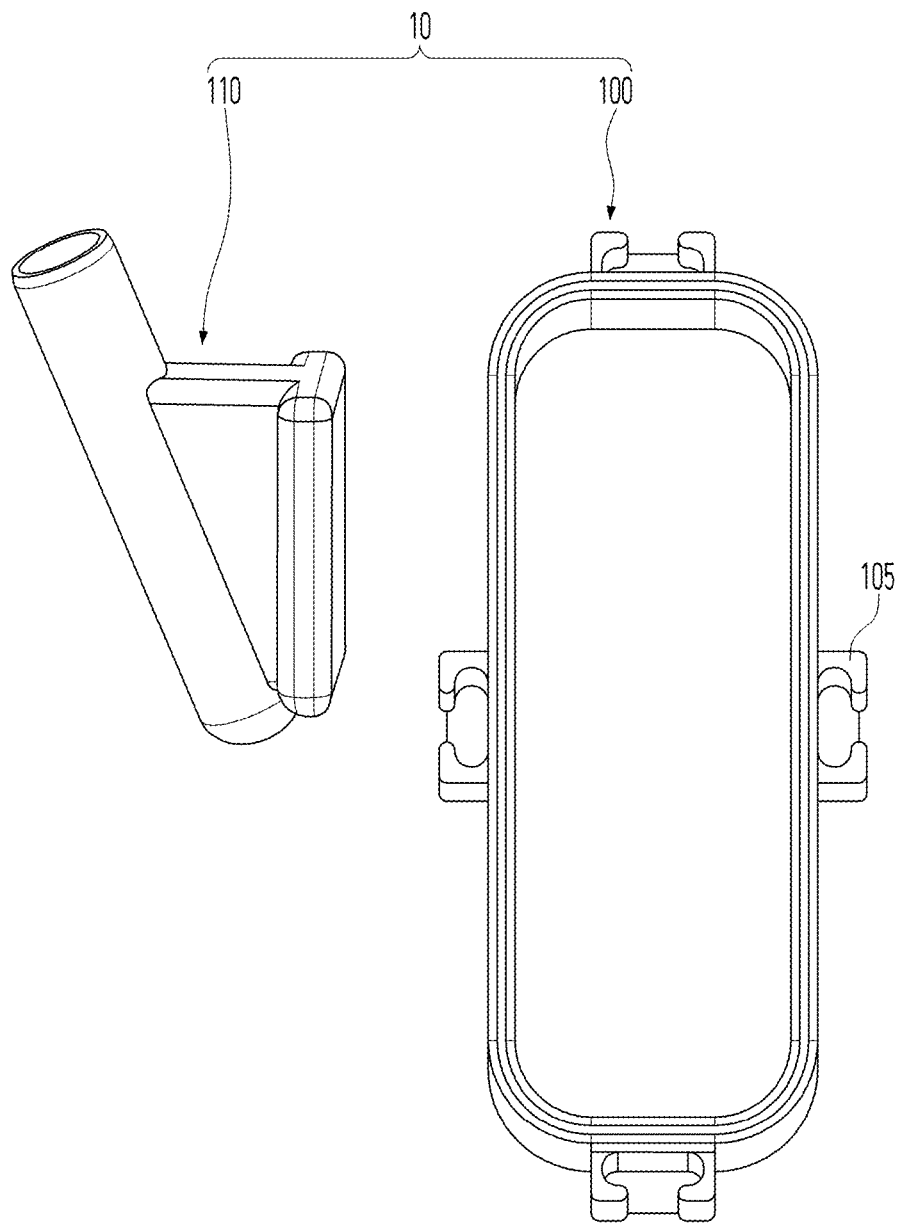
FIG. 3 is an exploded view of a probe detachable injection assistant, broken down into a probe holder and needle guide.

FIG. 1 is a top view of a probe detachable injection assistant according to one embodiment of the present disclosure, FIG. 2 is a side view of a probe detachable injection assistant according to one embodiment of the present disclosure, and FIG. 3 is an exploded view of a probe detachable injection assistant broken down into a probe holder and needle guide.

There are many cases in which ultrasound devices are used in medical practice, and in this case, the handle or the like of the ultrasound device is called a probe, and the probe detachable injection assistant according to the present disclosure corresponds to an assistant that can be detached or attached to the probe, but fixes a syringe.

In the course of an intervention using ultrasonography, it is sometimes necessary to perform an injection intervention on the human body while observing the screen with the probe (1) in contact with the human body, and when performing an injection intervention guided by ultrasonography, it is necessary to change the position of holding the syringe (2) while recognizing the blood vessel and injecting, and it is necessary to move the probe (1) or the syringe (2) to reposition it.

As can be seen with reference to FIGS. 1 through 3, a probe detachable injection assistant (10) may include a probe fixture (100) for holding the probe (1, not shown) and a needle guide (110) for holding a syringe.

According to one embodiment of the present disclosure, the probe fixture (100) and the needle guide (110) may be integrally formed, or each may be formed as a separate, independent object and interconnected therewith.

A probe detachable injection assistant (10) may form a plurality of needle guides (110). Therefore, it is possible to integrally mount or independently remove a plurality of needle guides (110) on one probe fixture (100), and the needle guides (110) can be coupled to any of the four sides (front, back, left side, right side) of the probe fixture (100).

A probe detachable injection assistant (10) according to the present disclosure, which is the device for fixing the probe (1, not shown), may be made of a resilient and elastic silicone material, but is not limited thereto and may also be made of other resilient or elastic materials.

Since a probe detachable injection assistant (10) is made of a resilient or elastic material as described above, it is naturally possible to adjust the width of a probe fixture (100) to fit the size of the probe (1). This allows for a high degree of contact with the probe (1) and an increased sense of security.

A probe fixture (100) may be mounted and secured to the probe (1) in such a way that it wraps around all or part of the outer circumferential surface of the probe (1). The outer circumferential surface of the probe fixture (100) has at least one receiving groove (105) formed therein for being coupled or seated of a bump (115) of the needle guide (110), which will be described below.

In other words, as the bump (115) is coupled with the receiving groove (105), the needle guide (110) is engaged to the probe fixture (100), thereby forming the probe detachable injection assistant (10) according to one embodiment of the present disclosure.

In one example, the receiving groove (105) may be designed to be horizontally movable along an outer circumferential surface of the probe fixture (100). Thus, in such a case, it is possible for the user to freely adjust the position of the receiving groove (105) within the outer circumferential surface of the probe fixture (100), thereby enabling the user to couple the needle guide (110) with the probe fixture (100) in a particular desired position.

On the other hand, the probe fixture (100) may be formed by being limited to a thickness of a predetermined specific size. In this case, the predetermined specific size thickness may preferably be 2 mm to 3 mm, which is specified as a thickness that can support or be supported by the needle guide (110) coupled to the receiving groove (105) without causing discomfort to the user while using the ultrasound probe (1).

In other words, the reason for thus limiting the probe fixture (100) to a certain predetermined thickness is that, when formed with a limited thickness, the volume and weight of the probe fixture (100) itself is also reduced, with the effect that the ultrasound probe (1) can always be used with the probe fixture (100) already coupled to the ultrasound probe (1).

In other words, in the past, the operator (or medical professional) did not always use the syringe guide, etc. coupled with the ultrasound probe (1), and when the syringe guide, etc. was needed during the ultrasound examination, the operator (or medical professional) separately coupled the syringe guide, etc. to the ultrasound probe (1) and used it, but after the injection was completed, the coupled syringe guide, etc. was removed from the ultrasound probe (1), which was inconvenient.

In the course of actual use, even in ultrasound examinations that do not directly utilize or need to utilize the function of the probe fixture (100) or the syringe guide, if the probe fixture (100) or the syringe guide is left attached to the ultrasound probe (1) as it is, the weight, bulkiness, or thickness of the probe fixture (100) or the syringe guide may cause the operator (or medical professional) to feel considerable constraint or discomfort in using the ultrasound probe (1), and mistakes or errors may occur in intervention using ultrasonography requiring precise operation.

On the other hand, since the present disclosure limits the probe fixture (100) to a certain predetermined thickness, the volume and weight of the probe fixture (100) itself is also reduced, and as a result, it is possible to use said ultrasound probe (1) with the probe fixture (100) always attached to said ultrasound probe (1) without causing any inconvenience or difficulty to the operator (or medical professional).

Furthermore, since the ultrasound probe (1) can be used with the probe fixture (100) always attached, it is not necessary to perform a separate process of attaching the probe fixture (100) at the moment when it is necessary to directly utilize the function of the probe fixture (100), which has the effect of maximizing the convenience of the operator (or medical professional) compared to the prior art.

Figure 4:
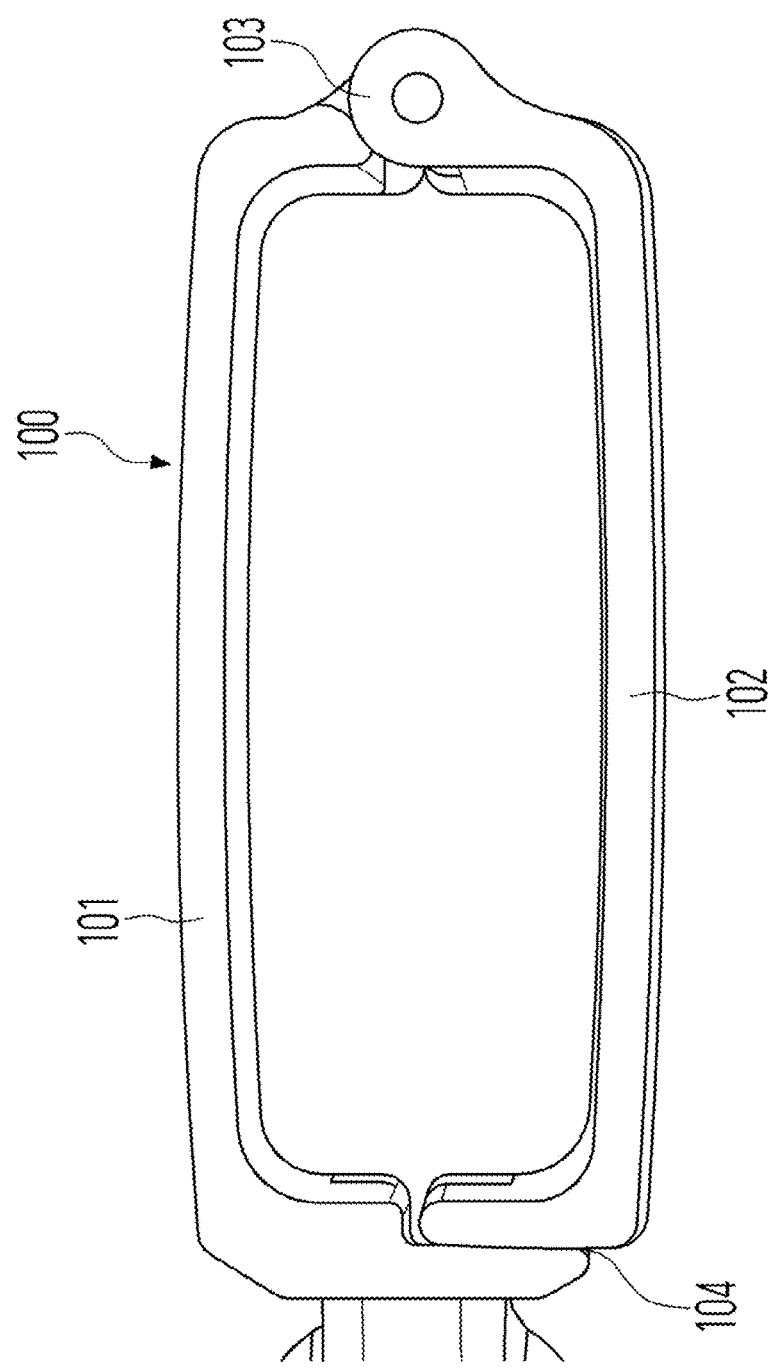
FIG. 4 is a drawing illustrating a probe fixture of a probe detachable injection assistant.
Figure 5:
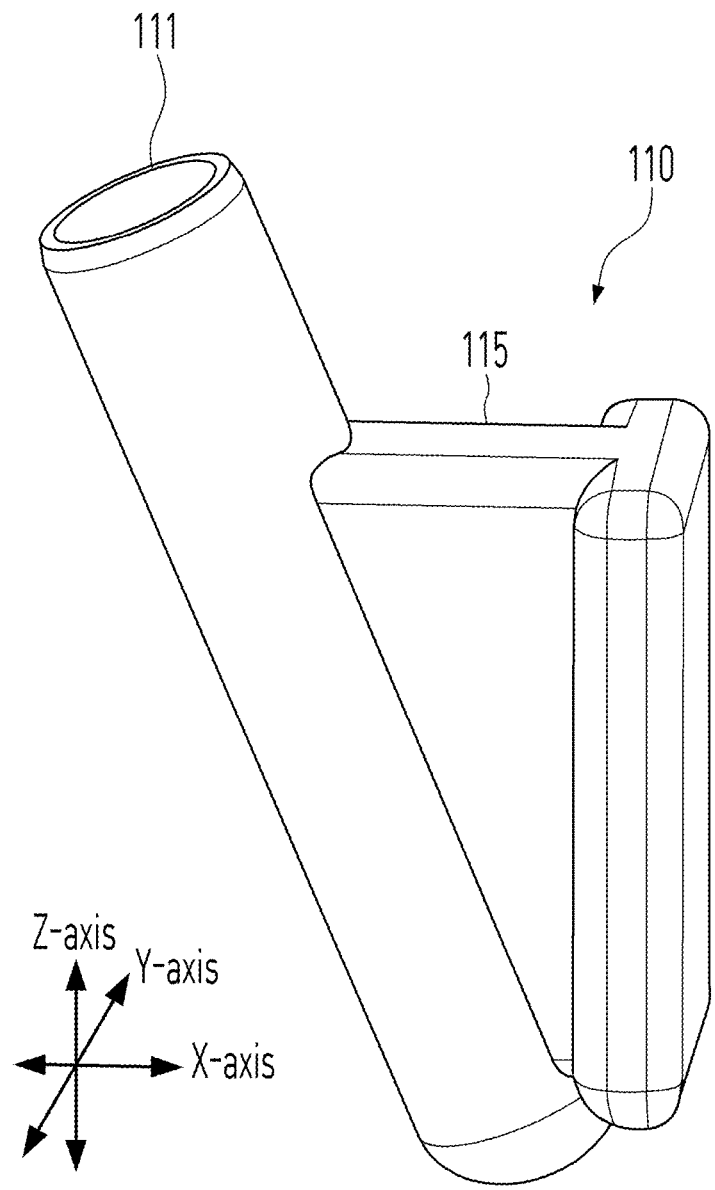
FIG. 5 is a drawing illustrating a needle guide of a probe detachable injection assistant.
Figure 6:
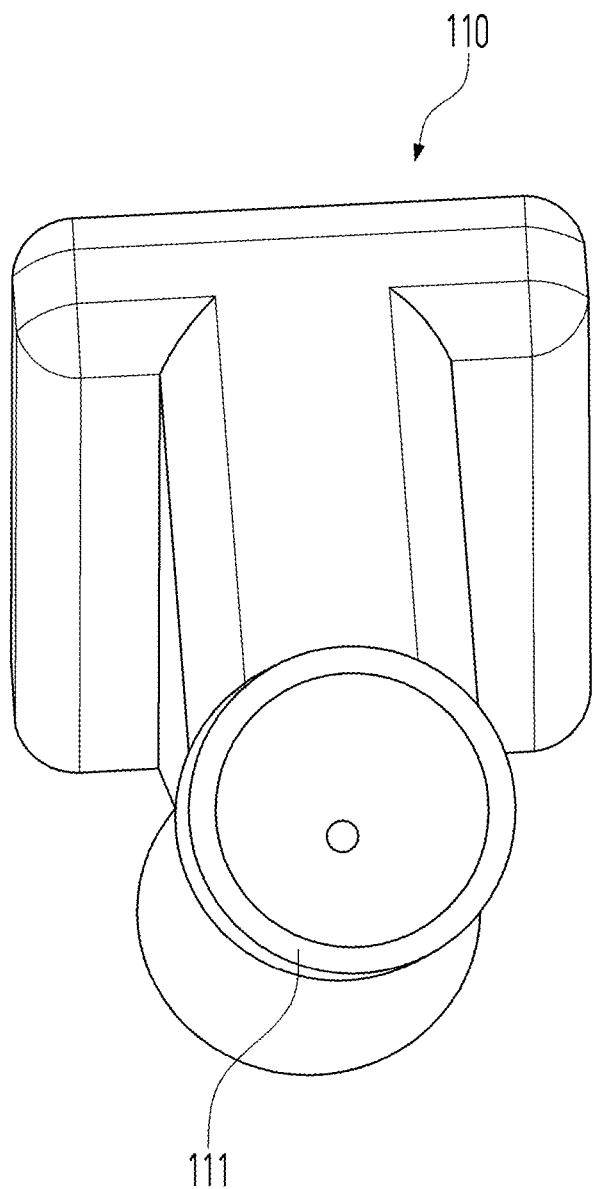
FIG. 6 is a top view of a needle guide of a probe detachable injection assistant.
Figure 7:
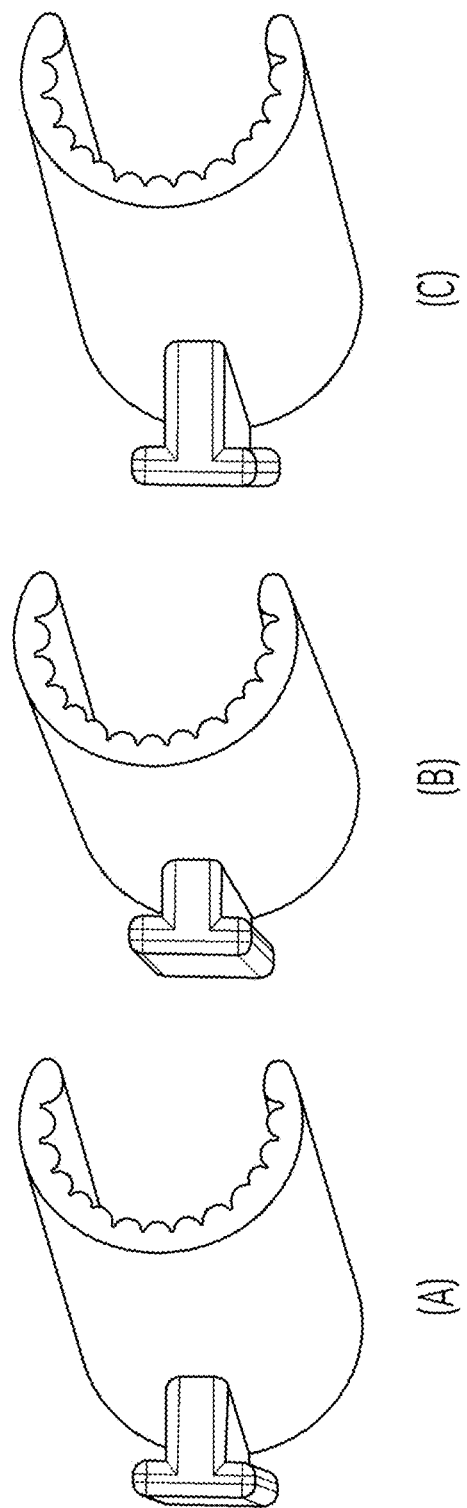
FIG. 7 is a drawing illustrating different types of needle guides.
Figure 8:
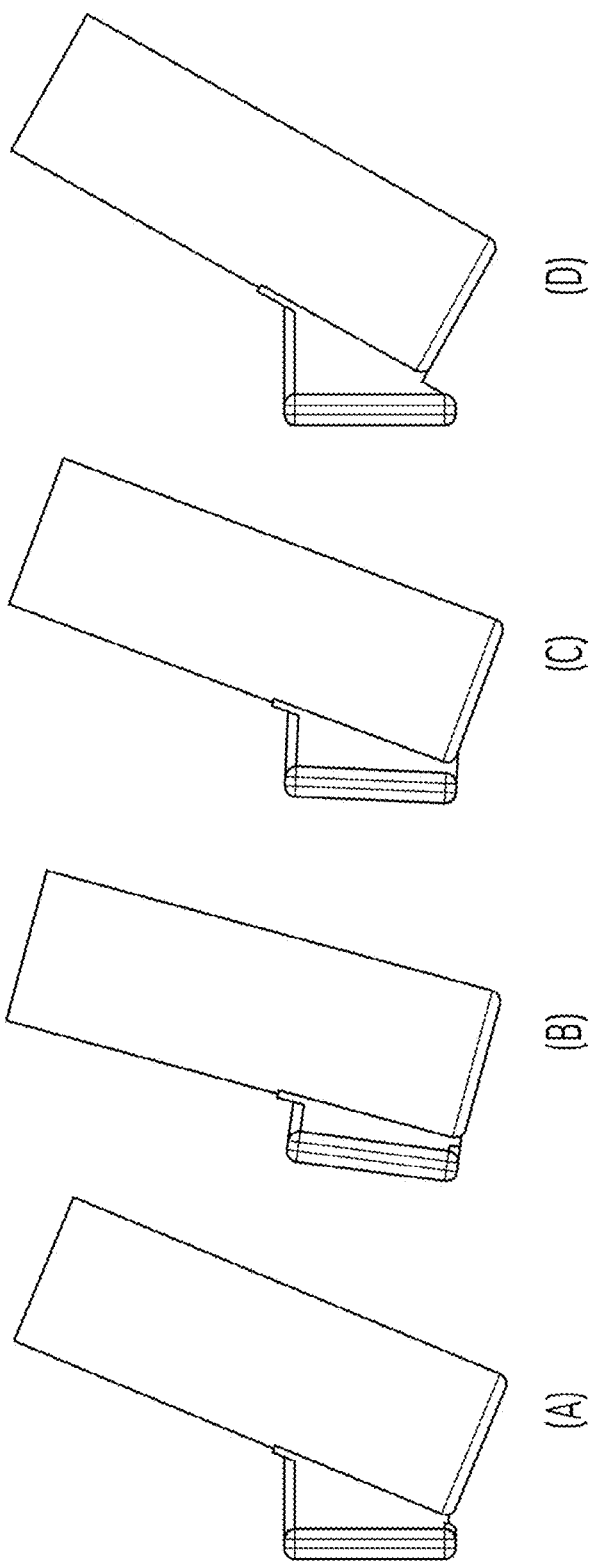
FIG. 8 is a drawing illustrating needle guides having different angles.
Figure 9:
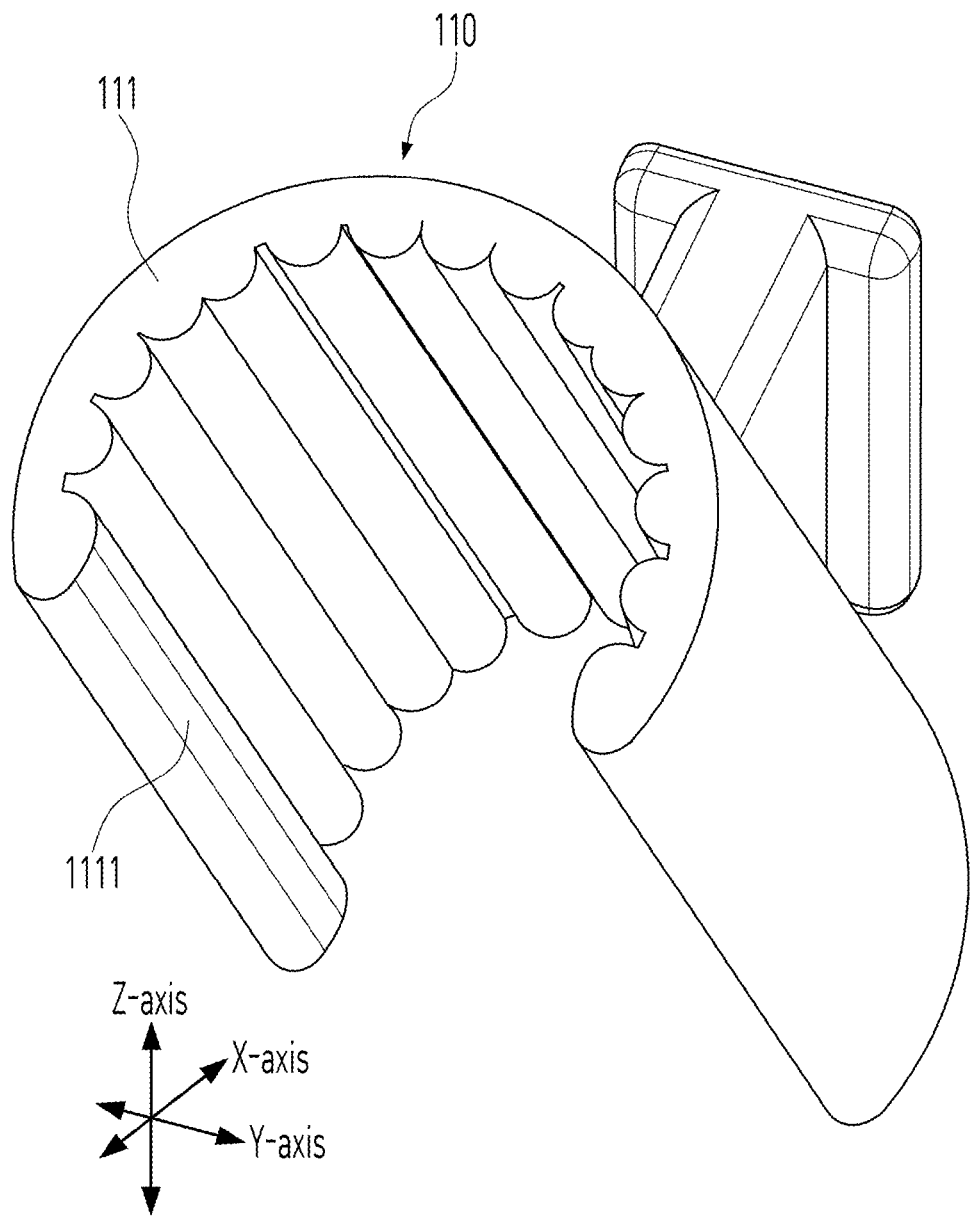
FIG. 9 is a drawing illustrating the interior of a needle guide.

FIG. 4 is a drawing illustrating a probe fixture of a probe detachable injection assistant, FIG. 5 is a drawing illustrating a needle guide of a probe detachable injection assistant, FIG. 6 is a top view of a needle guide of a probe detachable injection assistant, FIG. 7 is a drawing illustrating different types of needle guides, FIG. 8 is a drawing illustrating needle guides having different angles, and FIG. 9 is a drawing illustrating the interior of a needle guide.

Referring particularly to FIG. 4, a probe fixture (100) may be formed including a first body portion (101) and a second body portion (102). In one example, a probe fixture (100) may be formed to have an annular shape due to the coupling of a first body portion (101) and a second body portion (102) that are having a frame shape.

The first body portion (101) and the second body portion (102) may be coupled by a first connecting portion (103) and a second connecting portion (104). In one example, the first connecting portion (103) may correspond to a hinge coupling or a bolt/nut coupling, and the second connecting portion (104) may correspond to a latch coupling of the first body portion (101) and the second body portion (102).

A probe fixture (100) is horizontally adjustable in length to surround the outer circumferential surface of the probe (1) and to be secured to the probe (1). In one example, the first body portion (101) and the second body portion (102) are each adjustable in length to surround the outer circumferential surface of the probe (1) when coupled to each other.

On the other hand, a needle guide (110) according to the present disclosure is capable of inserting and holding a syringe (2). Furthermore, it is hingedly coupled with the probe fixture (100) so that the injection angle of the syringe (2) can be adjusted.

With respect to the injection angle of the syringe (2), a needle guide (110) may include a plurality of needle guides (110) formed at different angles, each or part of which may be coupled to the probe fixture (100), and furthermore, each of the needle guides (110) may be individually adjustable with respect to the injection angle.

The needle guide (110) may have a bump (115) formed thereon to be coupled to the receiving groove (105) of the probe fixture (100) described above. In one example, the bump (115) may, in the process of being coupled to the receiving groove (105) of the probe fixture (100), move along a guide formed in the receiving groove (105), thereby creating a sliding coupling between the bump (115) and the receiving groove (105).

On the other hand, the needle guide (110) may include a rail (111) formed to allow the syringe (2) to be inserted and to adjust the depth of insertion to control the depth of injection into the human body.

In one example, the rail (111) may have a shape such as a through-hole. In one example, the rail (111) may hold the body of the syringe (2) itself, but alternatively, it may hold only the needle.

The needle guide (110) is formed substantially including a rail (111) and a threshold (115), wherein the angle at which the rail (111) forms with respect to a vertical line with respect to the ground can control or modify the injection angle of the syringe (2). The rail (111) can be detached/attached from/to the needle guide (110), so that the probe detachable injection assistant (10) of the present disclosure can be used to facilitate injection in narrow or curved areas of the body.

In one example, as shown in FIG. 7, a plurality of protrusions (1111) may be formed inside the rail (111) to facilitate the insertion of the syringe (2) along the inner circumferential surface of the rail (111). The circular protrusions (1111) can be made to guide the syringe (2) inside the rail (111), where the syringe is secured and inserted, to facilitate sliding the syringe (2) up or down with the needle guide (110) coupled to the probe fixture (100). This has the effect that the depth of the syringe (or needle) being inserted into the body can be precisely controlled. As another example, the rail (111) may be made of titanium or stainless steel, which has the advantage of being easily disinfected after use, thus allowing repeated reuse.

In some embodiments, the protrusion (1111) includes a structure that allows air to enter the interior. In one example, the protrusions (1111) may correspond to a tube shape that allows air to enter the interior. Thus, the size of the interior space of the rail (111) can be adjusted as the protrusions (1111) expand and contract with the flow of air.

Accordingly, syringes of different volumes can be secured in perfect contact with the needle guide (110) by varying the size of the inner space of the rail (111), resulting in a more stable syringe insertion.

As another example, the diameter of the rail (111) and the length of the outer circumferential surface can be varied, so that the size of the rail (111) itself can be adjusted, and the size of the needle guide (110) can be varied accordingly to suit the size of the syringe.

In another example, the lower portion of the needle guide (110) can also be retractable, i.e., when the syringe (2) is not in use and the syringe (2) is coupled to the needle guide (110), the lower portion can be closed to prevent the needle portion of the syringe (2) from protruding outside of the rail (111), thereby preventing an unexpected incident of the needle from stabbing the human body. Conversely, when the syringe (2) is used, the lower portion of the needle guide (110) can be opened to allow the needle to protrude outside the rail (111) and perform an injection intervention into the human body.

Figure 10:
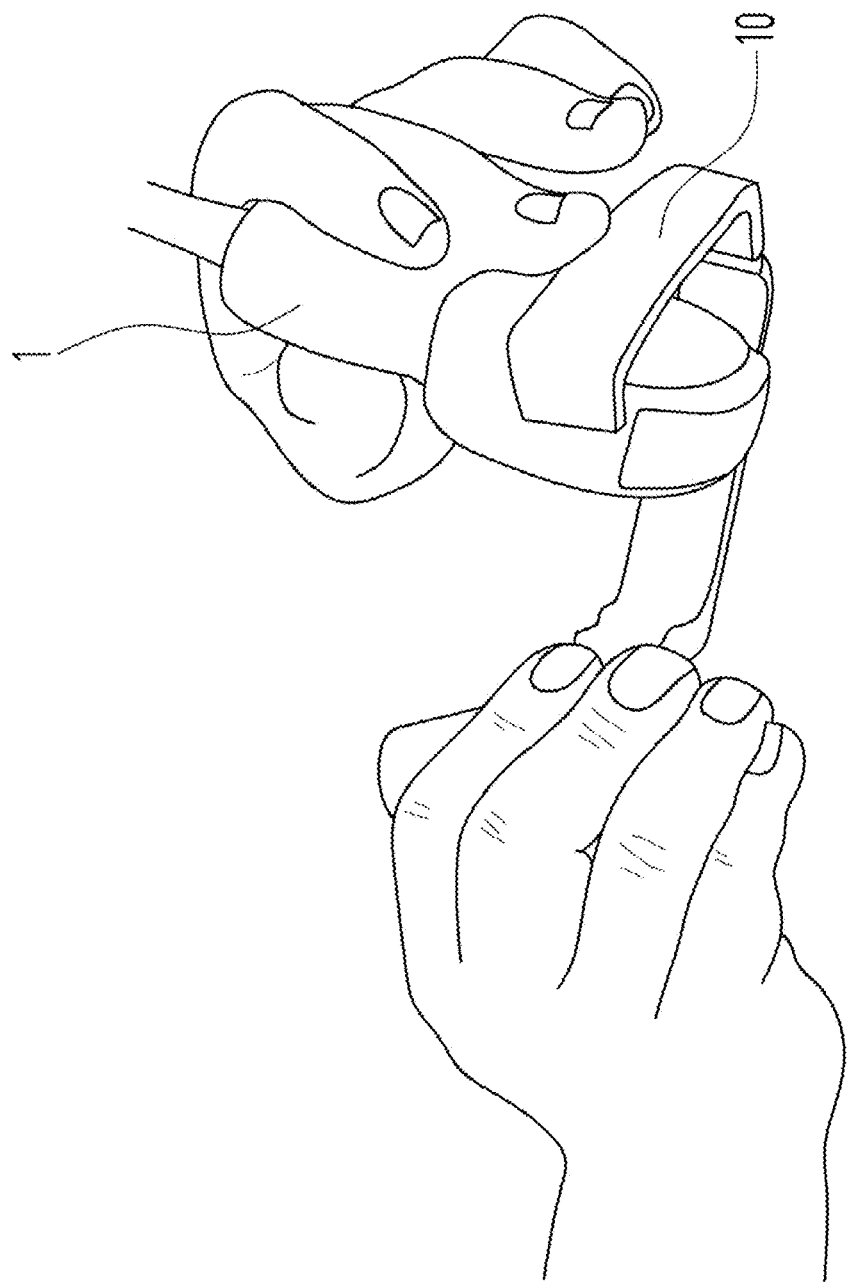
FIG. 10 is a drawing illustrating a probe detachable injection assistant according to one embodiment of the present disclosure as it is actually used to hold a probe.
Figure 11:
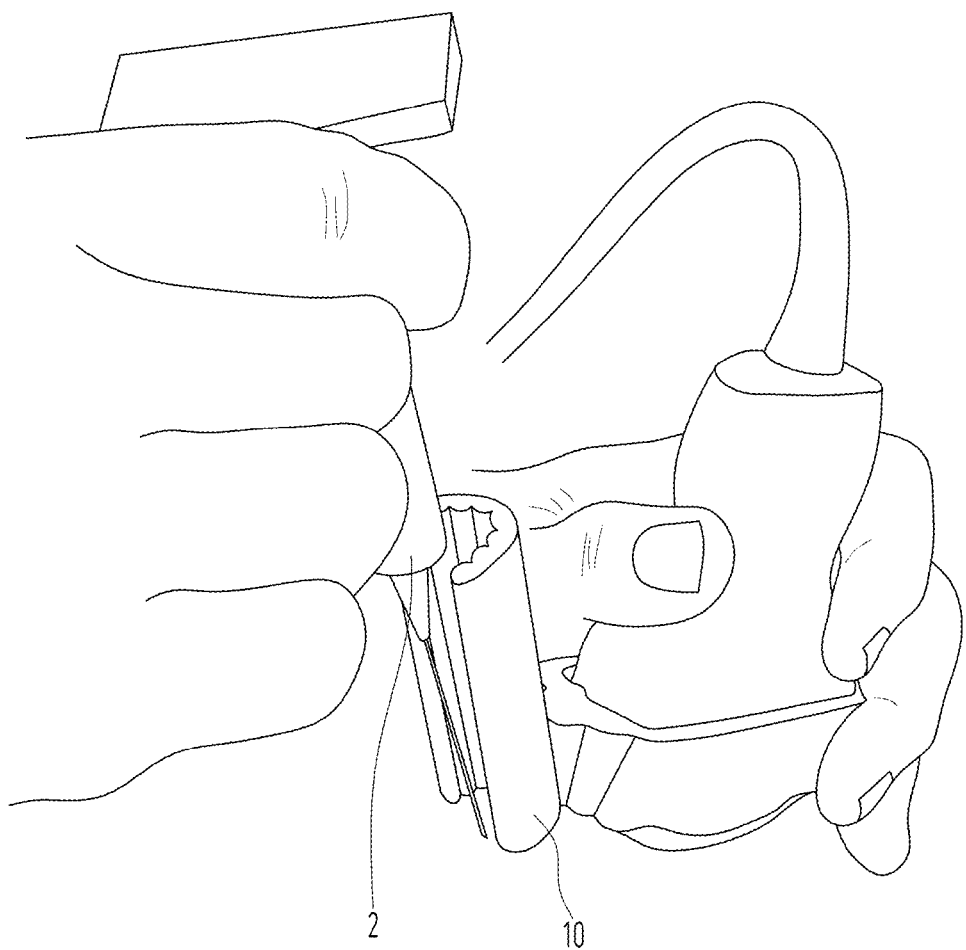
FIG. 11 is a drawing illustrating a probe detachable injection assistant according to one embodiment of the present disclosure as it is actually used to hold a syringe.

FIG. 10 is a drawing illustrating a probe detachable injection assistant according to one embodiment of the present disclosure as it is actually used to hold a probe, and FIG. 11 is a drawing illustrating a probe detachable injection assistant according to one embodiment of the present disclosure as it is actually used to hold a syringe.

FIG. 10 illustrates a probe detachable injection assistant (10), including a probe fixture (100) and a needle guide (110) made of silicone, being secured to and used with an ultrasound probe (1) in practice. FIG. 11 corresponds to an experimental example showing the inserted and secured syringe (2) in the needle guide (110), wherein it can be seen that the direction and depth of injection into the human body depends on the angle that the needle guide (110) makes with the human body and the position in which the syringe (2) is fixed, i.e., which part of the syringe is gripped by the needle guide (110).

Figure 12:
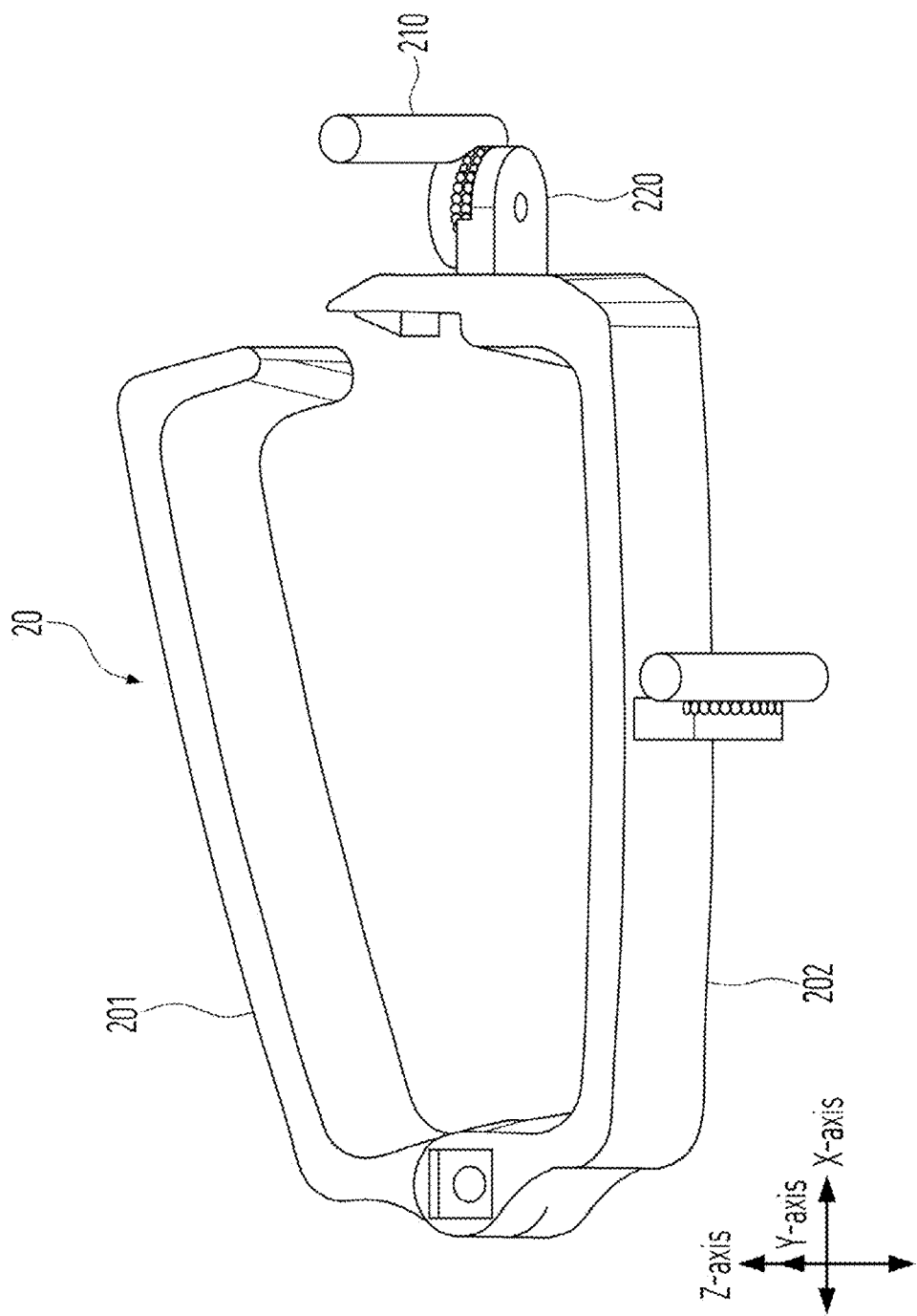
FIG. 12 is a perspective view of a probe detachable injection assistant according to another embodiment of the present disclosure.
Figure 13:
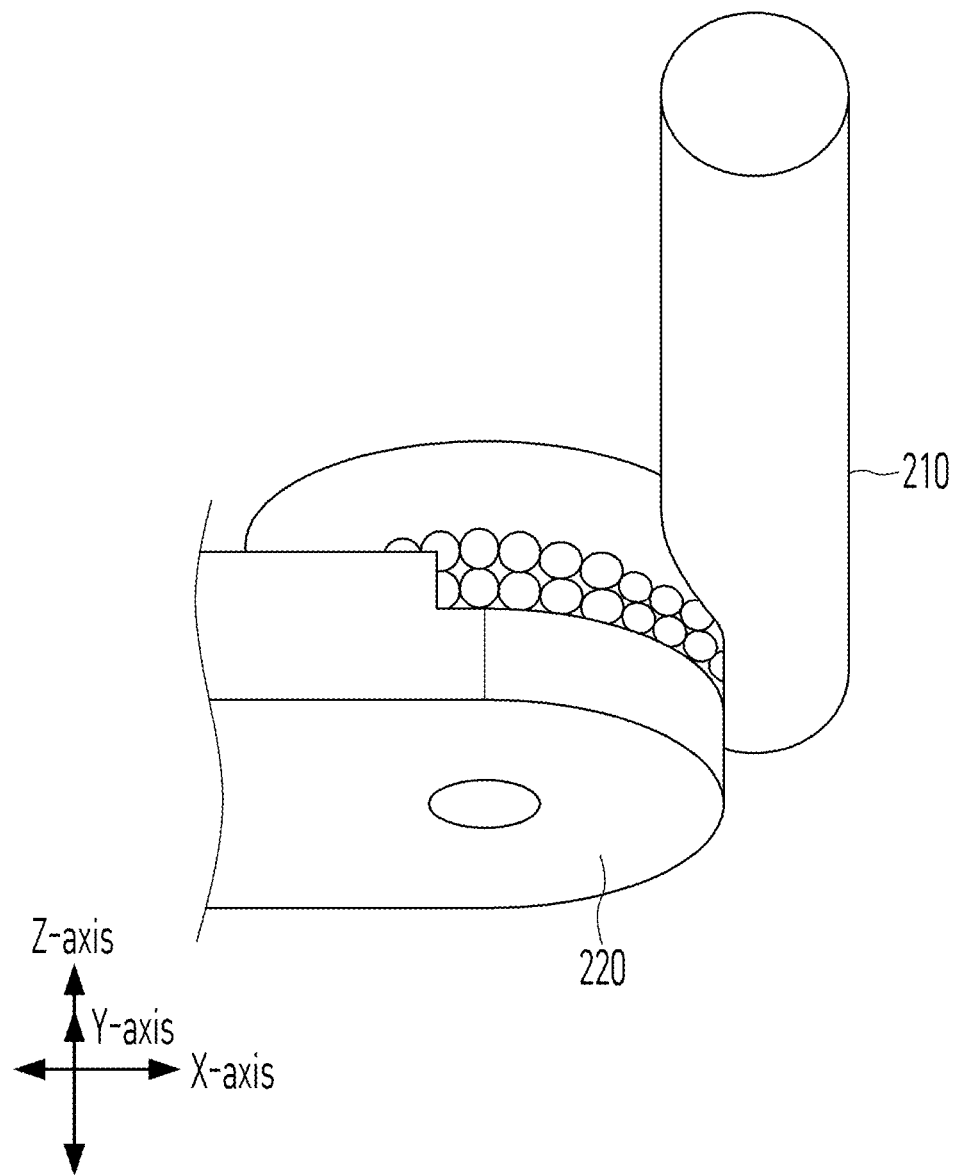
FIG. 13 is a drawing illustrating a needle guide of the probe detachable injection assistant of FIG. 12.

FIG. 12 is a perspective view of a probe detachable injection assistant according to another embodiment of the present disclosure, and FIG. 13 is a drawing illustrating a needle guide of the probe detachable injection assistant of FIG. 12.

The second probe detachable injection assistant (20), according to one embodiment of the present disclosure, may include a second probe fixture (200) that grips the lower portion of the ultrasound probe (1) along an outer circumferential surface and holds the probe (1) in place.

In one example, a second probe fixture (200) is formed by coupling the first frame (201) with the second frame (202), and may be secured to the ultrasound probe (1) in the form of a band or a ring.

The second probe detachable injection assistant (20) includes at least one second needle guide (210) formed on one side of the second probe fixture (200) and included to hold a needle of the syringe (2). The second needle guide (210) may further include an angle adjustment device (220) that enables the injection angle of the syringe (2) to be adjusted.

The second needle guide (210) of the second probe detachable injection assistant (20) corresponds to a tool that secures the movement of only the needle portion of the syringe, and not the entire syringe (2), when the needle of the syringe (2) is inserted in plane or out plane into the human body.

Thus, a second needle guide (210) can be coupled to the second probe fixture (200) and used by inserting and withdrawing only the needle into and out of the hole contained in the needle guide (210).

In this case, the angle adjustment device (220), which is capable of adjusting an angle, may have a preset and fixed angle adjustment. In one example, the angle adjustment device (220) may be in the form of a click, and each time a click is adjusted, the angle can be adjusted to a certain preset size.

In one example, the angle adjustment can be 10 degrees of tilt for each click adjustment. This has the advantage of allowing to determine in advance the depth of the needle that will be picked up by the ultrasound.

In one example, the depth of the hole formed in the second needle guide should be at least 3 cm to reduce and prevent errors caused by bending of the needle during insertion of the needle into the human body.

When the second probe detachable injection assistant (20) is used, it has the effect that the ultrasound probe (1) can also be fixed in position at the insertion point.

The above description is merely an exemplary description of the technical ideas of the present disclosure, and those having ordinary knowledge in the technical field to which the present disclosure belongs will be able to make various modifications and variations without departing from the essential features of the present invention.

Accordingly, the embodiments disclosed herein are intended to illustrate and not to limit the technical ideas of the present invention, and the scope of the technical ideas of the invention is not limited by these embodiments.

The scope of protection of the present disclosure shall be construed in accordance with the following claims, and all technical ideas within the scope of the equivalents thereof shall be construed to be included within the scope of the present disclosure.

DESCRIPTION OF SYMBOLS

1: Probe
2: Syringe
10: Probe detachable injection assistant
100: Probe fixture
101: First body portion
102: Second body portion
103: First connecting portion
104: Second connecting portion
105: Receiving groove
110: Needle guide
111: Rail
1111: Protrusion
115: Bump
20: Second probe detachable injection assistant
200: Second probe fixture
201: First frame
202: Second frame
210: Second needle guide
220: Angle adjustment device

The invention claimed is:

1. A structure of an ultrasound probe detachable injection assistant, comprising:
   a probe fixture for holding the ultrasound probe;
   wherein the probe fixture wraps around a portion of outer circumferential surface of the probe and is capable of securing the ultrasound probe, wherein the probe fixture is formed by a first body portion and a second body portion coupled by a first connecting portion and a second connecting portion, wherein the first body portion and the second body portion each being adjustable in length so as to wrap around outer circumference of the ultrasound probe when coupled,
   a plurality of needle guides for inserting and holding a syringe, and hingedly coupling with the probe fixture to allow adjustment of an injection angle of the syringe;
   a bump formed on each of plurality of needle guides for coupling the needle guides with the probe fixture;
   a receiving groove formed on at least one outer circumferential surface of the probe fixture to allow the bump to couple;
   a rail formed on each of the plurality of needle guides along which the syringe is inserted and which is adjustable to regulate a depth of injection into a human body by adjusting a depth of insertion; and
   a plurality of protrusions formed along an inner circumferential surface inside the rail to guide the securing and insertion of the syringe;
   wherein each of the plurality of protrusions comprises-a tubular structure that allows air to enter the interior, and wherein a size of the space inside the rail changes as each of the plurality of protrusions expand and contract.

2. The structure of claim 1, wherein the receiving groove is horizontally translatable along at least one of the outer circumferential surface of the probe fixture.

3. The structure of claim 1, wherein a lower portion of each of the plurality of needle guides is retractable.

4. The structure of claim 1,
   wherein the bump moves along a guide formed in the receiving groove, and wherein a sliding coupling is formed between the bump and the receiving groove.

5. The structure of claim 1, wherein each of the plurality of needle guides comprises an angle adjustment device for adjusting the injection angle of the inserted syringe, wherein the angle adjustment device is implemented in a click adjustment manner, wherein each adjustment of the click by a space results in a predetermined, constant magnitude change in the injection angle.

* * * * *